United States Patent
Sommer

(10) Patent No.: US 6,335,463 B1
(45) Date of Patent: Jan. 1, 2002

(54) METHOD OF MANUFACTURING SERTINDOLE

(75) Inventor: Michael Bech Sommer, Bagsvaerd (DK)

(73) Assignee: H. Lundbeck A/S, Valby-Copenhagen (DK)

( * ) Notice: Subject to any disclaimer, the term of this patent is extended or adjusted under 35 U.S.C. 154(b) by 0 days.

(21) Appl. No.: 09/423,096

(22) PCT Filed: May 7, 1998

(86) PCT No.: PCT/DK98/00183

§ 371 Date: Nov. 12, 1999

§ 102(e) Date: Nov. 12, 1999

(87) PCT Pub. No.: WO98/31685

PCT Pub. Date: Nov. 19, 1998

Related U.S. Application Data

(60) Provisional application No. 60/046,011, filed on May 9, 1997.

(30) Foreign Application Priority Data

May 9, 1997 (DK) .............................................. 0536/97

(51) Int. Cl.[7] ....................... C07C 229/00; C07D 233/22
(52) U.S. Cl. ....................... 562/454; 548/333.5; 514/323
(58) Field of Search ...................... 562/454; 548/333.5; 514/323

(56) References Cited

U.S. PATENT DOCUMENTS 4,710,500 A   12/1987   Perregaard ................... 514/254

OTHER PUBLICATIONS

Perregaard, J.K, et al., J. Med. Chem., 35:1092–1101, 1992.
Perregaard, J.K. et al., Dansk Kemi, 76:3:14–15, 1995.

*Primary Examiner*—Paul J. Killos
(74) *Attorney, Agent, or Firm*—Darby & Darby

(57) ABSTRACT

The present invention relates to a new method of manufacturing the compound 1-[2-[4-[5-chloro-1-(4-fluorophenyl)-1-H-indol-3-yl]-1-piperidinyl]ethyl]-2-imidazolidinone having the recommended INN name sertindole and a new method of manufacturing the intermediates, N-(4-fluorophenyl)-N-(2-carboxy-4-chlorophenyl)glycine and 5-chloro-1-(4-fluorophenyl)-3-(1,2,3,6-tetrahydropyridin-4-yl)indole used in the method.

37 Claims, No Drawings

METHOD OF MANUFACTURING SERTINDOLE

This application claims priority under 35 U.S.C. §119(e) of U.S. provisional application Ser. No. 60/046,011, filed May 9, 1997.

This Application is a 371 PCT/DK98/00183 filed May 7, 1998 which claims benefit of Provisional application Ser. No. 60/046,011, filed May 9, 1997.

BACKGROUND OF THE INVENTION

Sertindole is a well known antipsychotic drug having the formula

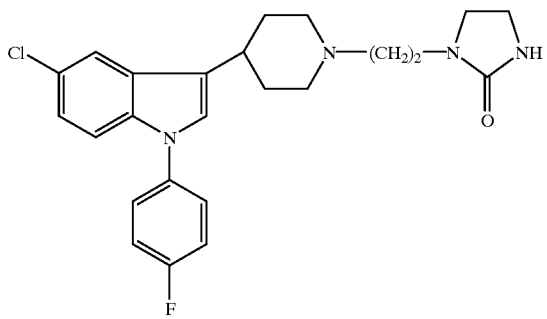

The compound was disclosed in U.S. Pat. No. 4,710,500 and the antipsychotic activity thereof was described in U.S. Pat. No. 5,112,838. Sertindole is a potent centrally acting 5-$HT_2$ receptor antagonist in vivo and has further been disclosed to be active in models indicative of effects in the treatment of anxiety, hypertension, drug abuse and cognitive disorders. Recently, it has been reported to show antipsychotic effect in clinical studies, *Psychopharmacology* (1996) 124:168–175.

U.S. Pat. No. 4,710,500 covered a class of 1-aryl-3-(piperazinyl-, tetrahydropyridyl or piperidyl)indole compounds including sertindole. A number of methods of preparing the compounds were generically disclosed, some of which could be used in the preparation of sertindole. The methods were:

a) reaction of a properly substituted 1-arylindole with a proper 1-substituted 4-piperidone and subsequent reduction of the resulting tetrahydropyridyl compound;

b) arylation of the corresponding 1-unsubstituted indole compound;

c) reduction of the corresponding compound having an oxo group in the 2-position of the indole ring.

Sertindole was specifically exemplified, however, no experimental procedure for its preparation was given.

Perregaard et al., *J Med. Chem*, 1992, 35, 1092–1101, disclosed a new method of preparing sertindole. This method comprises reaction of the intermediate 5-chloro-1-(4-fluorophenyl)indole with 4-piperidone in a mixture of trifluoroacetic acid and acetic acid, reduction of the resulting 5-chloro-1-(4-fluorophenyl)-3-(1,2,3,6-tetrahydropyridin-4-yl)indole in order to obtain 5-chloro-1-(4-fluorophenyl)-3-(piperidin-4-yl)indole which in turn is reacted with 1-(2-chloroethyl)-2-imidazolidinon in the presence of $K_2CO_3$ and KI in methyl isobutyl ketone (MIBK). The 5-chloro-1-(4-fluorophenyl)indole was obtained from the corresponding 3-acetoxy-indole by $NaBH_4$ reduction in methanol and subsequent elimination of $H_2O$ under acidic conditions. The 3-acetoxy-indole was prepared from the N-(4fluorophenyl)-N-(2-carboxy-4-chlorophenyl)glycine following literature procedures.

A procedure for preparing the N-(4fluorophenyl)-N-(2-carboxy-4-chlorophenyl)glycine is described in Perregaard et al.,*Dansk Kemi*, 95, 3. p. 6–9. By this method the glycine is obtained by a copper catalyzed reaction of 2,5-dichlorobenzoic acid with N-(4-fluorophenyl)glycine. The potassium salts of the two acids are used in the presence of $K_2CO_3$ in the solvent N-methylpyrrolidone (NMP).

However, it has been found that the above processes are not useful in technical scale. The total yields are too low and the processes involve the use of reactants or solvents that are not suitable and in some cases not allowed in large scale for environmental or safety reasons. Furthermore, due to the aqueous solubility of NMP, the work-up of the reaction is tedious, and regeneration of NMP is costly and time consuming.

Consequently, the present invention relates to a new process useful in technical scale production of sertindole.

It has now been found that the main limiting steps of the process are the preparation of N-(4-fluorophenyl)-N-(2-carboxy-4-chlorophenyl)glycine and the reaction of 5-chloro-1-(4-fluorophenyl)indole with 4piperidone.

Accordingly, the present invention provides a process for the preparation of N-(4-fluorophenyl)-N-(2-carboxy-4chlorophenyl)glycine comprising reaction of an alkalimetal salt of 2,5-dichlorobenzoic acid with an alkalimetal salt of N-(4-fluorophenyl)glycine in an aqueous, alkaline environment in the presence of a copper catalyst followed by treatment with an aqueous acid, as illustrated in the following reaction scheme:

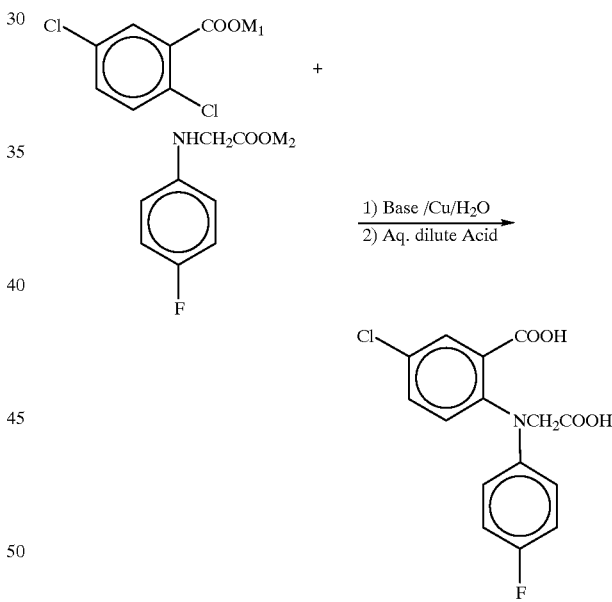

wherein M, and $M_2$ are alkali metal ions.

According to Perregaard et al.,*Dansk Kemi*, 95, a reaction using the potassium salts of the reactants is carried out in NMP. However, the use of NMP necessitated a time consuming extractive work-up, and the reaction afforded substantial amounts of tarry by-products. The reaction temperature was 120–130° C.

By carrying out the reaction in aqueous environment instead of NMP, a higher yield and only a negligible amount of tarry by-products are obtained. Furthermore, the work-up procedure is simple and the use of an aqueous medium causes substantial environmental advantages. Finally, the reaction temperature is lowered to the reflux temperature of the aquous medium or below.

In another aspect the invention provides a novel process for preparing 5-chloro-1-(4-fluorophenyl)-3-(1,2,3,6-tetrahydropyridin-4-yl)indole comprising reaction of the 5-chloro-1-(4-fluorophenyl)indole with 4-piperidone in a mixture of a mineral acid and acetic acid, as illustrated in the following reaction scheme:

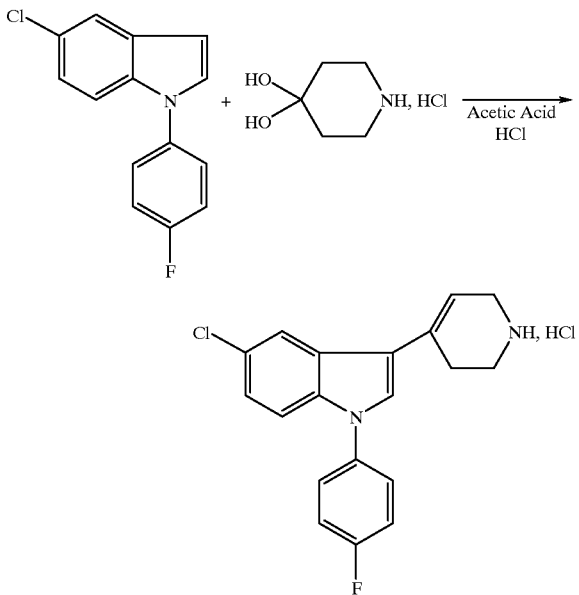

By using a mixture of acetic acid and a mineral acid instead of a trifluoroacetic acid-acetic acid mixture, substantial environmental advantages are obtained. Furthermore, trifluoro acetic acid is very volatile and aggressive, accordingly being undesirable for large scale production. Also, the formation of the undesired bis-substituted piperidine may be avoided:

Formula I

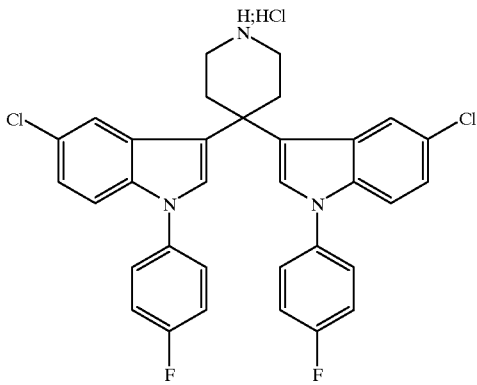

In yet another aspect, the invention provides a novel process of manufacturing sertindole comprising preparation of N-(4fluorophenyl)-N-(2-carboxy4-chlorophenyl)glycine by a reaction comprising a copper catalysed reaction of an alkalimetal salt of 2,5-dichlorobenzoic acid with an alkali metal salt of N-(4-fluorophenyl)glycine in an aqueous, alkaline environment in the presence of a copper catalyst and/or in which 5-chloro-1-(4-fluorophenyl)-3-(1,2,3,6-tetrahydropyridin-4-yl)indole is obtained by a reaction comprising reaction of the 5-chloro-1-(4-fluorophenyl)indole with 4-piperidone in a mixture of a mineral acid and acetic acid.

The reaction of the alkalimetal salt of 2,5-dichlorobenzoic acid with the alkalimetal salt of N-(4-fluorophenyl)glycine is carried out at an elevated temperature, conveniently at a temperature between 80° C. and the reflux temperature of the medium, preferably at about the reflux temperature. Throughout the specification and claims the term aqueous medium is intended to include water and water to which a cosolvent such as ethyleneglycol is added as reaction medium. Preferably water such as demineralised, deionised or destined water is used.

Preferred alkali metal salts of the reactants are the lithium, sodium or potassium salts and conveniently the same salts of the reactants are used. Most preferably the potassium salts are used.

It is important that the HCl formed during the reaction is neutralised in order to avoid undesired side reactions. The reaction medium is made alkaline by addition of a base such as an alkali metal hydroxide, alkali metal acetate, alkali metal carbonate, alkali metal hydrogen carbonate, alkali metal phosphate or alkali metal citrate. Preferably an alkali metal carbonate, such as $Li_2CO_3$, $Na_2CO_3$ or $K_2CO_3$, is used. Conveniently, the same alkali metal as included in the reactants is used. Preferably the base is potassium carbonate. The amount of base is preferably larger than the stoechiometric amount of 2,5-dichlorobenzoic acid. On the other hand, increased [OH] may cause hydrolysis of 2,5-dichlorobenzoic acid, thereby decreasing the yield. Thus, the base may conveniently be added gradually during the process.

The catalyst may be any Cu(0)-catalyst, preferably copper-bronze. It is added in catalytic amounts. The specific amount is not critical and may easily be determined by a person skilled in the art.

The ratio between the amounts of the alkali metal salt of N-(4-fluorophenyl)glycine and the alkali metal salt of 2,5-dichlorobenzoic acid is conveniently from 0.5 to 3.0, preferably 1.0 to 2.5 and most preferably 2.0 to 2.3 mol/mol. Excess N-(4-fluorophenyl)glycine may be regenerated.

The reaction is conveniently carried out in a minimal amount of aqueous solvent still technically feasible. Thus, the yield is improved by decreasing the amount of solvent. The amount of water is preferably less than 10 mL/g 2,5-dichlorobenzoic acid, more preferably less than 5 mL/g in particular less than 3.5 mL/g, most preferably less than 2.5 mL/g.

The reaction time is not very critical and may easily be determined by a person skilled in the art.

The work-up of the product by dilute aqueous acid may be carried out simply by adding the filtered reaction mixture to the dilute acid, thereby precipitating the product. The product may be further purified with hot toluene or by recrystallization from aqueous ethanol. The dilute aqueous acid is preferably hydrochloric acid.

In the reaction of the 5-chloro-1-(4-fluorophenyl)indole with 4-piperidone, the mineral acid used is preferably phosphoric acid, nitric acid, sulfuric acid or hydrochloric acid, such as larger than 30% w/w aqueous HCl, in particular concentrated hydrochloric acid. By concentrated HCl is meant about 37% w/w aqueous HCl.

The 4-piperidone is preferably used as the 4-piperidone-hydrate, hydrochloride.

The reaction should preferably be carried out in excess of piperidone-hydrate hydrochloride. Preferably more than 1.5 equivalents of 4-piperidone pr equivalent 5-chloro-1-(4-fluorophenyl)indole, more preferably more than 1.75, are used. Conveniently, 2.0 equivalents are used.

It is important that sufficient acid is present to allow a sufficient yield. When hydrochloric acid is used as mineral acid, it is preferably used in an amount of at least 2.5 mL concentrated HCl pr. g 5-chloro-1-(4-fluorophenyl)indole. Most preferably the ratio is 3.5 to 5 mL concentrated HCl pr. g 5-chloro-1-(4-fluorophenyl)indole.

The amount of acetic acid has to be sufficient to make the reaction technically feasible. Conveniently, at least 8 mL acetic acid pr. g 5-chloro-1-(4-fluorophenyl)indole is used. Preferably, the amount of acetic acid is more than 10 mL acetic acid pr. g 5-chloro-1-(4-fluorophenyl)indole, most preferably 10–14 mL. The ratio between acetic acid and concentrated HCl is preferably 2:1 to 4:1 vol/vol. The reaction is conveniently carried out by adding, drop-wise, a solution of the 5-chloro-1-(4-fluorophenyl)indole in hot acetic acid to the piperidone-hydrate, hydrochloride or by mixing the two reactants in a mixture of acetic acid and mineral acid followed by reflux. The reaction time is easily determined by a person skilled in the art.

The intermediate may be worked up in a conventional manner. The further process leading to sertindole comprises cyclization of N-(4-fluorophenyl)-N-(2-carboxy-4-chlorophenyl)glycine to the corresponding 3-acetoxy-indole using eg. acetic anhydride in the presence of alkalimetal acetate such as sodium acetate. 5-chloro-1-(4-fluoro)indole is then obtained from the 3-acetoxy-indole by reduction and subsequent elimination of $H_2O$. The resulting 5-chloro-1-(4-fluorophenyl)indole is reacted with 4-piperidone according to the above procedure, the resulting 5-chloro-1-(4-fluorophenyl)-3-(1,2,3,6-tetrahydropyridin-4-yl)indole is reduced in order to obtain 5-chloro-1-(4-fluorophenyl)-3-(piperidin-4-yl)indole which in turn is reacted with 1-(2-chloroethyl)-2-imidazolidinon to obtain sertindole. Alternatively, the 5-chloro-1-(4-fluorophenyl)-3-(1,2,3,6-tetrahydropyridin-4-yl)indole may first be reacted with 1-(2-chloroethyl)-2-imidazolidinon followed by reduction, thereby obtaining sertindole, which may be isolated as an acid addition salt, e.g. the tartrate, or as the free base.

The alkalimetal salt of 2,5-dichlorobenzoic acid and the alkalimetal salt of N-(4-fluorophenyl)glycine used as starting materials are easily prepared from commercially available 2,5-dichlorobenzoic acid and N-(4-fluorophenyl)glycine, respectively, by standard procedures.

Sertindole, as obtained by the process, may conveniently be formulated as described in U.S. Pat. No 5,112,838.

EXPERIMENTAL SECTION

Example 1

Preparation of N-(4-fluorophenyl)-N-(2-carboxyphenyl)glycin

A suspension comprising potassium 2,5-dichlorobenzoate (100 g, 0.44 mol, 1 eq.), potassium N-(4-fluorophenyl)glycinate (190 g, 0.92 mol, 2.1 eq.), potassium carbonate (36.2 g, 0.26 mol, 0.6 eq. $CO_3^-$), copper bronze (2.8 g, 0.04 mol Cu, 0.1 eq.) and 250 mL demineralised water was heated at reflux under $N_2$ atmosphere for 20.5 hours and then cooled to 50° C.

2.5 mL water and 5 g activated carbon were added to the reaction mixture which, except for the Cu-bronze, was homogeneous. The mixture was allowed to cool under stirring for 1 hour and filtered. The filter cake was washed with 2×125 mL water. The filtrate was poured on a mixture of ice (2 L) and 37% aq. HCl (3–400 mL) under vigorous stirring, thereby crystallising the crude product as a fine, crystalline, yellow-brown material. The suspension was stirred at 75–80° C. for 30 min, cooled to 15–20° C., and filtered, and the filter cake was washed with 500 mL water and dried under air stream over night at 50° C. The filtrate was collected for regeneration of N-(4-fluorophenyl)glycinate.

Yield of crude product: 113 g (80.3%), mp. 170–86° C.

HPLC-analysis: 84.2% w/w product, 10.5% w/w 3-chlorosalicylic acid.

20 g of the above dry crude product was further purified by suspension in 200 mL toluene and reflux for 30 min. The suspension was allowed to cool to room temperature under stirring and was then filtered. The filter cake was washed with toluene (20 mL) and dried overnight in vacuum at 50° C.

Yield: 17.0 g, mp. 190–92° C. Purity>98% as detemined by NMR-analysis.

Example 2

Preparation of N-(4-fluorophenyl)-N-(2-carboxyphenyl)glycin 21.0 kg potassium 2,5-dichlorobenzoate was added to a 180 L reactor and 36.0 L water was added. This mixture was heated under stirring until substantially all solids were dissolved (temp 60–70° C.) and 25.0 kg potassium N-(4-fluorophenyl)glycinate was added slowly. The mixture was heated until all materials were dissolved, i.e. at about 80° C. and added to a mixture of 7.67 kg $K_2CO_3$, 582 g Cu-bronze and 7 L water. The combined mixture was refluxed overnight (about 15 h) and cooled to 50° C. 1 kg activated carbon suspended in 5 L water was added followed by 40 L water. The mixture was stirred under cooling for 1 hour, and filtered on a nutch covered with filter aid. The filter cake was washed with 10 L water and the green filtrate was slowly during about 2 hours poured on a mixture of 22.5 L 37% HCl and 30 L water under gentle heating (45–50° C.) and stirring. The mixture was heated to 72° C., cooled to 25° C. and filtered. The filter cake was washed with water (2×10 L) and dried on trays overnight at 60° C. Yield 26.7 kg of a pale yellow crystalline crude product.

The crude product, 26.7 kg, was transferred to a 200 L reactor and 150 L toluene added and the mixture was heated to the reflux temperature (90° C.) under $N_2$ cover. Then the mixture was destilled until a temperature of 110° C. was reached (5 L distillate). 5 L toluene was added, and the mixture was refluxed at 110° C. for 2 hours, cooled to about 60° C. and left overnight at 27° C. The mixture was filtered and the filter cake was washed with toluene (3×15 L) and dried, thereby obtaining 21.0 kg of the pure title product.

Example 3

1-(4-flourophenyl)-3-acetoxy-5-chloroindole

N-(4-flourophenyl)-N-(2-carboxyphenyl)glycin (717.1 g, 2.22 mol), sodium acetate (36.4 g, 0.44 mol, 0.2 eq.) and acetic anhydride were placed in a 4 L three necked flash equipped with mechanical stirrer and reflux condenser.

The suspension was heated under stirring until reflux. The reaction mixture was refluxed for 1 hour and was cooled to room temperature on ice/water bath. The homogenous suspension was under stirring poured onto ice (2 L) and was neutralised with concentrated NaOH (appr. 6 L) until a pH of 6–7. During the neutralisation the temperature was kept under appr. 30° C., which required the adding of a further 5–6 L of ice. Thereby the product precipitated and was isolated by filtration. The product was washed thoroughly with 3 L of water and 2 L of n-Heptane and dried over night in vacuum at 60° C.

Yield: 600.5 g (89.1%), mp 109–12° C.

Example 4

1-(4-fluorophenyl)-5-chloroindole 1-(4-flourophenyl)-3-acetoxy-5-chloroindole (100.0 g, 0.33 mol) was dissolved in 1000 mL EtOH. During the next hour sodium borohydride pellets (18.7 g, 1.5 eq.) were added batchwise at reflux. The reaction mixture was stirred over night at reflux and cooled to room temperature. Concentrated HCl (appr. 50 mL until pH 1) was added and the reaction mixture was stirred at room temperature for 1 hour. 200 mL demineralized water was added, and the resulting suspension was filtrated. The filter cake was washed with further 50 mL water and 10 mL EtOH. The product was dried over night in vacuum at 50° C.

Yield: 68.4 g (84.7%), mp 91–93° C.

Example 5

Preparation of 5-chloro-1-(4-fluorophenyl)-3-(1,2,3,6-tetrahydropyridin-4-yl)indole 5-chloro-1-(4-fluorophenyl)indole (6.70 kg) and 4-piperidone-mono-hydrate,hydrochloride (8.38 kg) were transferred to a 200 L reactor under $N_2$ cover. Acetic acid (67 L) was added and the reaction mixture was heated to 60° C. Concentrated HCl (37%, 33.5 L) was added during ½ hour and then the mixture was heated to the reflux temperature (85° C.) and refluxed for 1 hour (final temperature 95° C.). After cooling to 30° C., 33.5 L acetone was added followed by further cooling to 25° C. Filtration, wash (acetone 20 L) and drying in vacuum at 60° C. gave the title product as a white powder, yield 8.94 kg.

Example 6

1-[2-[4-[5-chloro-1-(4-flourophenyl)-1H-indol-3-yl]-1,2,3,6-tetrahydro-1-pyridyl]ethyl]-2imidazolidinone 5-chloro-1-(4-fluorophenyl)-3-(1,2,3,6-tetrahydropyridin-4-yl)indole (6.0 kg. 16.5 mol), 1-(2-chloroethyl)imidazolon (3.19 kg, 1.3 eq.), sodium carbonate (anhydrous) and methyl isobutyl ketone (60 L) were mixed. The reaction mixture was heated under $N_2$-cover and stirring until 90–95° C., and was stirred over night at this temperature. The next day the reaction mixture was filtered while still hot. The apparatus and filter cake were washed with further 2.5 L of methyl isobutyl ketone. The combined filtrates were left over night for crystallisation. The product was isolated on a nutch, washed with 7.5 L n-Heptane and dried over night in vacuum at 60° C.

Yield: 5.39 kg (74.3%), mp 146.4° C.

Example 7

1-[2-[4-[5-chloro-1-(4-fluorophenyl)-1-H-indol-3-yl]-1-piperidinyl]ethyl]-2-imidazolidinone, tartrate 1-[2-[4-[5-chloro-1-(4-flourophenyl)-1H-indol-3-yl]-1,2,3,6-tetrahydro-1-pyridyl]ethyl]-2-imidazolidinone (3.5 kg) was dissolved in acetic acid (98–100%, 29 L) while being heated until 40° C. Activated carbon was added and the suspension was stirred for 1 hour, left over night and filtered. The filter cake was washed with 6 L acetic acid. The combined filtrates were added to a 50 L hydrogenation reactor which was covered by $N_2$. 70 g $PtO_2$ was added, the apparatus was closed and $N_2$ blown through for 5 min. Hydrogenation was carried out in an $H_2$-flow (2.5 L per min) for 8.25 H. The reaction mixture was blown through with nitrogen, activated carbon was added and the mixture was filtered on a closed nutch. The filtrate was combined with corresponding filtrates of three other hydrogenations (a total of 14.53 kg starting material) and evaporated in vacuum at appr. 50° C. The filtrate was flushed off with 3×10 L toluene at 50–60° C. The remenance was dissolved in 146 L ethanol and to this suspension a 40° C. suspension of 5.22 kg L–(+) tartaric acid in 16 L demineralised water was added under stirring. The suspension was left over night with no cooling or stirring. The crystallised tartrate was filtered on a nutch and washed with 15 L ethanol.

The crude tartrate was recrystallised from 190 L ethanol and 30 L demineralised water by heating until boiling (appr. 78° C.). The suspension was left over night for crystallasation with no cooling or stirring. The next day the suspension was cooled to appr. 18° C. and the tartrate was filtered off, washed with 60 L ethanol and dried over night under air stream at 60° C.

Example 8

1-[2-[4-[5-chloro-1-(4-flourophenyl)-1H-indol-3-yl]-1-piperidinyl]ethyl]-2-imidazolidinone 7.96 kg 1-[2-[4-[5-chloro-1-(4flourophenyl)-1H-indol-3-yl]-1,2,3,6-tetrahydro-1-pyridyl]ethyl]-2-imidazolodione, tartrate was suspended in 25 L demineralised water and 30 L dichloromethane was added. A total of 3 L 27% NaOH-solution, pH=9, was added to the suspension under stirring. The mixture was stirred for 1 hour (pH still=9), whereafter the dichloromethane phase was separated.

The water phase was extracted with further 15 L dichloromethane. The combined dichloromethane phases were dried with $NaSO_4$ and were evaporated. The product was flushed off with 5 L acetone, 35 L acetone was added and the suspension was heated until reflux. The crystallised product did not dissolve completely. Heating was discontinued and the mixture was left over night with gentle cooling. The crystallised product was isolated on a notch, washed with further 5 L acetone and dried over night under air stream at 60° C.

Yield: 4.90 kg (83.2%), mp 154.7° C.

What is claimed is:

1. A process for the preparation of N-(4-fluorophenyl)N-(2-carboxy-4-chlorophe-nyl)-glycine comprising a copper catalysed arylation of 2,5-dichlorobenzoic acid with N-(4-fluorophenyl)glycine in which alkalimetal salts of 2,5-dichlorobenzoic acid and N-(4-fluorophenyl)glycine are employed in an aqueous, alkaline environment in the presence of a copper catalyst according to the reaction scheme:

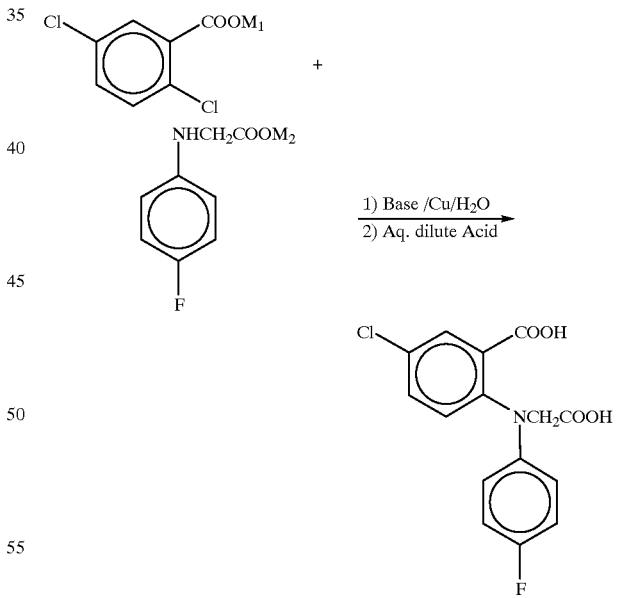

wherein $M_1$ and $M_2$ are alkali metal ions.

2. A process according to claim 1, characterised in that the reaction is carried out at a temperature between 80° C. and the reflux temperature of the medium.

3. A process according to claim 1, characterised in that the reaction medium is water or water to which a cosolvent is added.

4. A process according to claim 3, characterised in that water is used as solvent.

5. A process according to claim 3, characterised in that the amount of water is less than 10 mL/g 2,5-dichlorobenzoic acid.

6. A process according to claim 5, characterised in that the amount of water is less than 3.5 mL/g 2,5-dichlorobenzoic acid.

7. A process according to any of claim 1, characterised in that the alkalimetal salts used are the lithium, sodium or potassium salts.

8. A process according to claim 7, characterised in that the alkalimetal salts are potassium salts.

9. A process according to claim 1, characterised in that the base is an alkalimetal carbonate.

10. A process according to claim 9, characterised in that the alkalimetal of the alkali metal carbonate is the same as the alkalimetal of the reactants.

11. A process according to claim 1 characterised in that the base is potassium carbonate.

12. A process according to claim 1 characterised in that the amount of base is larger than the stoichiometric amount of 2,5-dichlorobenzoic acid.

13. A process according to claim 1 characterised in that the catalyst is copper-bronze.

14. A process according to claim 1 characterised in that the ratio between the amounts of the alkalimetal salt of N-(4-fluorophenyl) glycine and the alkali metal salt of 2,5-dichlorobenzoic acid is from 0.5 to 3.0 mol/mol.

15. A process for preparing 5-chloro-1-(4-fluorophenyl)-3-(1,2,3,6-tetrahydropyridin-4-yl)indole comprising reaction of 5-chloro-1-(4fluorophenyl)indole with 4piperidone in a mixture of a mineral acid and acetic acid.

16. Process according to claim 15, characterised in that the 4-piperidone is used in the form of 4-piperidone-hydrate, hydrochloride.

17. Process according to claim 15, characterised in that the mineral acid used is phosphoric acid, nitric acid, sulfuric acid or hydrochloric acid.

18. Process according to claim 17, characterised in that the mineral acid used is concentrated hydrochloric acid.

19. Process according to claim 15, characterised in that at least 1.5 equivalents of 4-piperidone is used pr. equivalent 5-chloro-1-(4-fluorophenyl)indole.

20. Process according to claim 19, characterised in that at least 1.75 equivalents of 4-piperidone is used pr. equivalent 5-chloro-1-(4-fluorophenyl)indole.

21. Process according to claim 20, characterised in that at least 2.0 equivalents of 4-piperidone is used pr. equivalent 5-chloro-1-(4-fluorophenyl)indole.

22. Process according to claim 18, characterised in that hydrochloric acid is used in an amount of at least 2.5 mL concentrated HCl pr. g 5-chloro-1-(4-fluorophenyl)indole.

23. Process according to claim 15, characterised in that at least 8 mL acetic acid pr. g 5-chloro-1-(4-fluorophenyl)indole is used.

24. Process according to claim 23, characterised in that at least 10 mL acetic acid is used pr. g 5-chloro-1-(4-fluorophenyl)indole.

25. Process according to claim 24, characterised in that 10–14 mL acetic acid is used pr. g 5-chloro-1-(4-fluorophenyl)indole.

26. Process according to claim 22, characterised in that the ratio is 3.5 to 5 mL concentrated HCl pr. g 5-chloro-1-(4-fluorophenyl)indole.

27. Process according to claim 18, characterised in that the ratio between acetic acid and concentrated HCl is 2:1 to 4:1 (vol/vol).

28. A process of manufacturing sertindole comprising preparation of N-(4-fluorophenyl)-N-(2-carboxy-4-chlorophenyl) glycine by a process of claim 1.

29. A process of manufacturing sertindole comprising a) preparation according to claim 1 of N-(4-fluorophenyl)-N-(2-carboxy-4-chlorophenyl)glycine, by reacting an alkalimetal salt of 2,5-dichlorobenzoic acid with an alkalimetal salt of N-(4fluorophenyl) glycine in an aqueous, alkaline environment in the presence of a copper catalyst;

b) cyclisation of N-(4-fluorophenyl)-N-(2-carboxy-4-chlorophenyl)glycine to the corresponding 3-acetoxy-indole using acetic anhydride/alkalimetal acetate, c) reduction of the 3-acetoxy-indole and subsequent d) elimination of $H_2O$ thereby obtaining 5-chloro-1-(4fluorophenyl)indole e) reaction of 5-chloro-1-(4fluorophenyl)indole with 4-piperidone according to any of claims 15–27 in a mixture of an acetic acid and concentrated HCl f) reduction of the resulting 5-chloro-1-(4-fluorophenyl)-3-(1,2,3,6-tetrahydropyri din-4-yl)indole in order to obtain 5-chloro-1-(4-fluorophenyl)-3-(piperidin-4-yl) indole g) reaction of the product of f) with 1-(2-chloroethyl)-2-imidazolidinon, or h) reaction of 5-chloro-1-(fluorophenyl)3-(1,2,3,6-tetrahydropyridin-4-yl)indole with 1-(2-chloroethyl)-2-imidazolidinon followed by reduction of the product, thereby obtaining sertindole.

30. A process according to claim 1, characterised in that the reaction is carried out at about the reflux temperature of the medium.

31. A process according to claim 5, characterised in that the amount of water is less than 5 mL/g 2,5-dichlorobenzoic acid.

32. A process according to claim 6, characterised in that the amount of water is less than 2.5 mL/g 2,5-dichlorobenzoic acid.

33. A process according to claim 1, wherein the base is selected from the group consisting of $Li_2CO_3$, $Na_2CO_3$ and $K_2CO_3$.

34. A process according to claim 1, characterised in that the ratio of alkalimetal salt of N-(4-fluorophenyl)glycine and the alkalimetal salt of 2,5-dichlorobenzoic acid is from 1.0 to 2.5 mol/mol.

35. A process according to claim 1, characterised in that the ratio of alkalimetal salt of N-(4-fluorophenyl)glycine and the alkalimetal salt of 2,5-dichlorobenzoic acid is from 2.0 to 2.3 mol/mol.

36. A process of manufacturing sertindole comprising preparation of 5-chloro-1-(4-fluorophenyl)-3-(1,2,3,6-tetrahydropyridine4-yl) indole according to claim 15.

37. A process according to claim 7, characterized in that the alkali metal salts are the same salts of the reactants used.

* * * * *

UNITED STATES PATENT AND TRADEMARK OFFICE
CERTIFICATE OF CORRECTION

PATENT NO. : 6,335,463 B1
DATED : January 1, 2002
INVENTOR(S) : Michael Bech Sommer It is certified that error appears in the above-identified patent and that said Letters Patent is hereby corrected as shown below:

<u>Title page,</u>
Item [87], PCT Pub. No., change "PCT Pub. No.: WO98/31685" to -- PCT Pub. No.: WO98/51685 --.

Signed and Sealed this

Fourth Day of June, 2002

*Attest:*

JAMES E. ROGAN
*Attesting Officer*  *Director of the United States Patent and Trademark Office*